United States Patent [19]

Yamada

[11] Patent Number: 5,564,565
[45] Date of Patent: Oct. 15, 1996

[54] DISPOSABLE HYPODERMIC NEEDLE RECEPTACLE

[76] Inventor: Todd H. Yamada, 13900 Tahiti Way, #127, Marina Del Rey, Calif. 90292

[21] Appl. No.: 306,262

[22] Filed: Sep. 14, 1994

[51] Int. Cl.⁶ .......................... A61M 5/32; B65D 83/10
[52] U.S. Cl. .......................... 206/365; 206/364; 604/192; 128/919
[58] Field of Search .................... 206/364, 364, 206/366, 370; 604/192, 198, 263; 128/919

[56] References Cited

U.S. PATENT DOCUMENTS

| | | | |
|---|---|---|---|
| 4,742,910 | 5/1988 | Staebler | 206/365 |
| 4,986,817 | 1/1991 | Code | 604/263 |
| 5,061,248 | 10/1991 | Sacco | 604/263 |
| 5,078,695 | 1/1992 | Farrar, Jr. et al. | 206/365 |
| 5,098,400 | 3/1992 | Crouse et al. | 604/192 |
| 5,183,469 | 2/1993 | Capuccio | 206/365 |
| 5,285,896 | 2/1994 | Salatka et al. | 206/366 |
| 5,334,151 | 8/1994 | Santilli | 206/365 |
| 5,347,078 | 9/1994 | Eckels | 206/365 |
| 5,368,580 | 11/1994 | Suzuki | 206/365 |
| 5,395,338 | 3/1995 | Gaba | 206/366 |

FOREIGN PATENT DOCUMENTS 9014116  11/1990  WIPO ...................... 128/919

Primary Examiner—Paul T. Sewell
Assistant Examiner—Marie Denise Patterson
Attorney, Agent, or Firm—Beehler & Pavitt

[57] ABSTRACT

A disposable receptacle for receiving and retaining for disposal a used hypodermic syringe comprising a body in the shape of the frustum of a pyramid and formed of two mating halves joined together along a vertical plane comprehending the pyramid axis, each half being molded of a light inexpensive plastic material and defining half of a orifice extending from the top of the pyramid down partially toward its bottom. Inside the upper rim of the orifice formed by joining the two halves is a recess provided with resilient means to permit the syringe cap to be passed into the orifice but retained against withdrawal therefrom. Thereby the syringe may be withdrawn from its cap for use and re-inserted after use for disposal with the receptacle body.

1 Claim, 1 Drawing Sheet

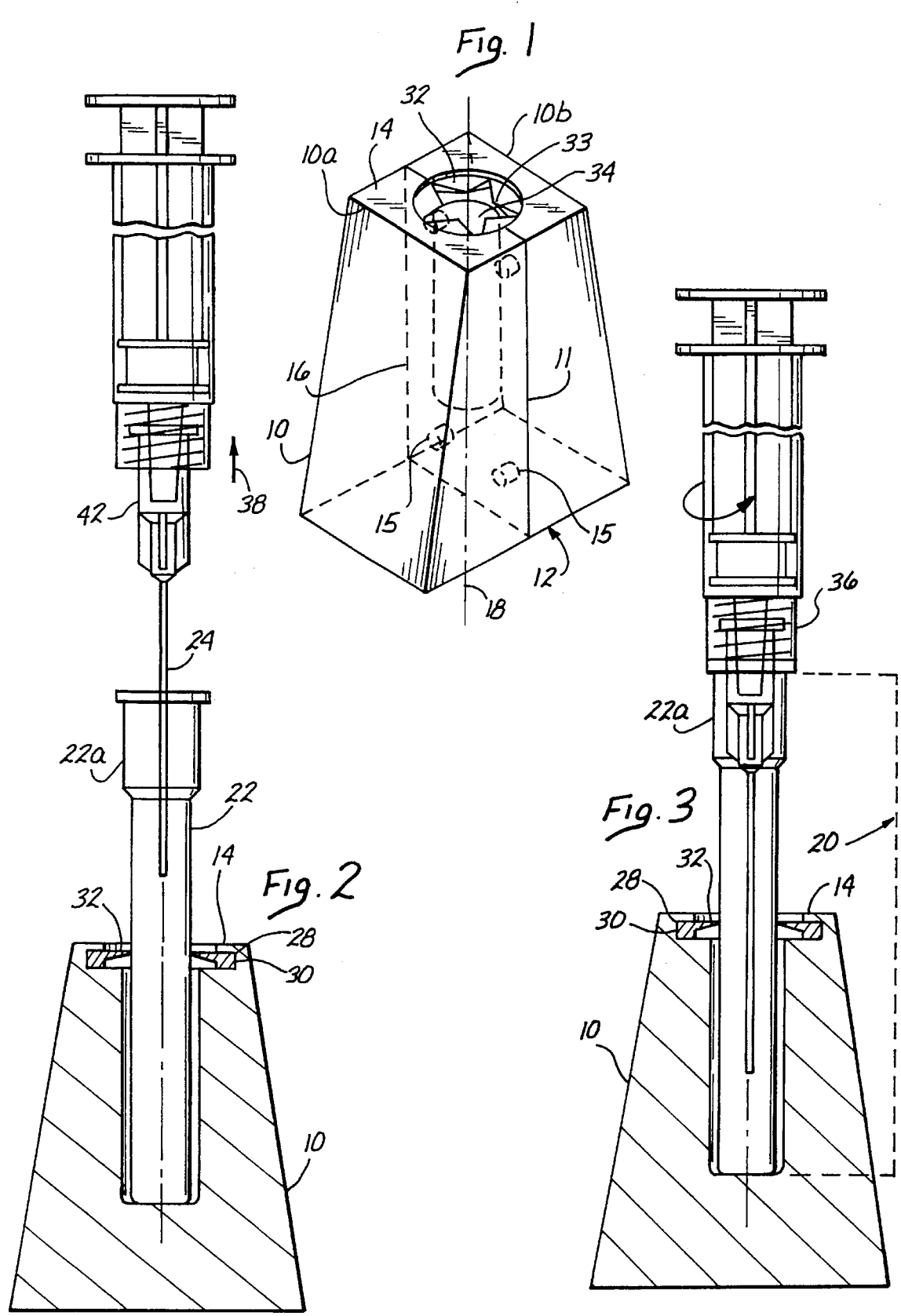

DISPOSABLE HYPODERMIC NEEDLE RECEPTACLE

FIELD OF THE INVENTION

This invention relates generally to medical and dental devices, and particularly to receptacles for the sanitary disposition of used hypodermic needle syringe.

BACKGROUND OF THE INVENTION

1. Description of the Prior Art

The removal and disposition of hypodermic needle syringes after the needles of such syringes have been inserted into and withdrawn from a patient's body member have always been a matter of concern in the medical and dental fields. Medical and dental personnel ordinarily take great pains to avoid being pricked or stuck by any such needle since it is possible through a rupture of the skin of any such personnel, for the latter to become infected with whatever bacteria or virus may be carried by the patient into whose body part the needle has been inserted and from which it has been withdrawn. With the recognition in recent years of the danger of becoming infected through a used needle with the HIV virus, the concern of those persons charged with removing needles from syringes after patient use has become almost phobic. No one wishes even to handle used syringes for disposition even in waste containers, or handling waste containers in which needles and/or syringes have been deposited. The concern is that if the handler has even a slight scratch or other breach in his or her own skin, whether caused by the needle itself or through some prior wounding, it could result in the virus passing into the bloodstream of the handler.

In an effort to avoid this possibility, a number of expedients have been devised, some of which, as disclosed in U.S. Pat. Nos. 4,454,944, 4,890,734, 4,892,191, 5,183,156 and 5,205,409, provide for containers to receive a number of syringe needles. A problem with such devices is that they may occupy a substantial amount of table or counter space and may not be dumped until the end of the day, or at some other convenient time. The containers themselves must then be carefully scrubbed, autoclaved or otherwise cleaned.

Recognizing the desirability of individual dispositions of needles themselves, U.S. Pat. Nos. 4,836,373 and 4,915,698 have disclosed angular hollow receptacles into which a needle may be inserted for deposit and retention. These devices, however, appear to require some means on their bases to secure them at the angles shown in the patent drawings. Also, because of their narrow mouth openings, inserting a needle and its cap into the devices may result in some "misses" which could result in the needle depositing some of its contaminant around the top of the device, or even pricking anyone holding the receptacle. These latter devices also appear to be expensive to manufacture so that it may be costly to the facility to use and throw away such a receptacle after each individual use. Also, they are not adapted for use with disposable syringes.

What is needed, therefore, is an inexpensive receptacle into which a disposable syringe with its needle may be easily and accurately inserted, which receptacle may be safely picked up and discarded as soon as the needle has been deposited within the receptacle.

SUMMARY OF THE INVENTION

The present invention provides an inexpensive disposable receptacle for a hypodermic needle syringe, which receptacle, because of its low cost may be immediately deposited in a medical trash container as soon as a used syringe has been inserted in it. The receptacle is formed as a body in the shape of the frustum of a pyramid of an inexpensive plastic, such as styrofoam, which is molded to provide a recess extending downwardly from the upper face of the styrofoam body. The latter is of an altitude in excess of a substantial portion of the cap provided to cover the hypodermic needle of a disposable syringe; and the recess is also slightly greater in depth than the said substantial portion of the cap. The recess is itself annularly recessed just below the upper face of the body to receive a circular disc having a plurality of yieldable prongs directed radially inwardly toward the axis of the recess, the tips of which prongs, however, are spaced far enough apart from each other about the axis to permit the needle cap, with the yielding of the prong tips to pass into the recess and retain it in that disposition. The cap is first deposited in the recess before the needle is used by inserting it in the patient's body member. After the needle has been so inserted in, and withdrawn from, the patient's body member, the needle and its base in the disposable syringe are pushed back into the syringe cap which has been deposited in the receptacle recess and is retained by the disc prongs. The body, the cap held in the recess and the disposable syringe the needle of which has been re-inserted into the cap, may immediately be deposited in some type of medical waste trash container.

DESCRIPTION OF THE DRAWINGS

FIG. 1 is a perspective view of the preferred embodiment of the invention.

FIG. 2 is a side elevation partly in section showing the body of FIG. 1 into which a needle cap has been inserted and a needle of the syringe being withdrawn from its cap.

FIG. 3 is a view similar to FIG. 2, but showing the syringe with its needle re-inserted in its cap which has been retained in the recess of the receptacle body.

DESCRIPTION OF THE PREFERRED EMBODIMENT

Referring to FIG. 1, a body 10 in the configuration of a frustum of a pyramid having a square base 12 and a parallel upper face 14, is molded of an inexpensive but rigid plastic, such as a polystyrofoam. Extending downwardly from the upper face 14 coaxial with the axis 18 of the body 10 is a recess 16. The altitude of the body 10 should be preferably at least a half an inch greater than half the length 20 of the cap 22 for the needle 24, and the altitude of the recess 16 should be at least a quarter of an inch less than the altitude of the body 10. The body 10 desirably is formed of two separate mating halves 10a, 10b, which are joined together in the plane 11, either by adhesive (not shown), or by interlocking pegs 15. When each half 10a, 10b is molded, provision is made for it to include one half of an annular recess 28 disposed below the upper face 14 of the body (FIG. 2 and FIG. 3) to receive a yieldable retainer disc 30 of either aluminum or plastic. This retainer disc 30 may have a plurality of radially inwardly extending prongs 32, the tips 33 of which are spaced from each other and may be of a configuration to define a star-shaped opening 34. The disc 30 may be slipped into the recess 28 before the halves 10a, 10b are joined together to form the body 10.

In use, a syringe 36 having a needle 24 and its cap 22 disposed on the nozzle 42 of the syringe is first inserted downwardly through the opening 34 in the disc 30 until about one half of the needle cap 22 passes the prongs 32, to seat in the recess 16 and be gripped by the prongs 32; whereupon the syringe needle 24 may be withdrawn from the cap 22 in the direction of the arrow 38 in FIG. 2, to leave the cap 22 held in the recess 34 by the prongs 32 of the disc 30. Although it may be necessary or desirable for the user of the receptacle to grasp the outer wall of the body 10 as the nozzle 42 is withdrawn from the cap 22, this poses no hazard to the user. After such withdrawal of the syringe nozzle 42 with the needle 24, the latter may be used on the patient following which the needle 24 is re-inserted into the cap 22 which is held by the prongs 32 of the disc 30, until the syringe nozzle 42 is locked back in the upper portion 22a of the cap 22. At this point, the body 10 with its entombed needle 24 and cap 22 carrying the syringe 36, may be simply picked up and thrown into a medical waste container (not shown).

Because of the ability to mold and join the body halves 10a, 10b with their recesses, of a very inexpensive plastic material and assemble them with a light inexpensive disc 30, the cost of providing and using this receptacle is minimized. Further, because of its frustum of a pyramid shape, the receptacle 10 of the present invention will be found to be extremely stable when placed on a counter or table, and to present no problem to the user of the hypodermic needle who simply passes the needle 24 and its cap 22 through the space 34 defined by the prongs 32 of the disc 30. The body 10 also occupies a minimal amount of space, so that it may be placed most conveniently on a table, counter or other horizontal surface in the immediate vicinity where the needle is being inserted in, and withdrawn from, the patient.

I claim:

1. In combination, a hypodermic syringe and a disposable receptacle for receiving and retaining for disposal the hypodermic syringe after use, said syringe comprising an elongated cylindrical portion having a first open end and a second open end adapted to carry fluid to be dispensed through a hollow needle, the base end of which needle is attached to the second open end of the cylinder, the opposite end of the needle having a tip for insertion in a preselected area of a patient's body, a plunger insertable in said cylinder through the first end and slideable toward the second end to force fluid provided in the cylinder out of the second end of the cylinder through the needle, means to attach the base end of the needle to the second end of the cylinder; and an elongated detachable plastic cap adapted to fit over and cover the needle from its tip to the means to secure the needle to the second end of the cylinder and removably interlock with the last means; and said receptacle comprising:

a body in the shape of the frustum of a pyramid having a height in the order of half the length of the detachable plastic cap of the syringe, said body being molded of a rigid, but light plastic material, and said body having a polygonal base lying in a first plane, and a corresponding upper face lying in a second plane parallel to the first plane and disposed below the projected apex of the pyramid, said upper face being similar to but of a smaller area than the polygonal base; and outer side walls extending between said base and said upper face, said outer side walls being slanted inwardly and upwardly toward each other to the said upper face, said upper face being axially recessed downwardly toward the base, said recess being defined by the side walls of the body, and of transverse dimension greater than the dimension of the cross section of the plastic cap of the syringe, and said recess extending axially into the body for a distance less than the height of the body, the upper area of said recess adjacent the upper face of the body being provided with means adapted to permit the plastic cap to be passed through the orifice only into, but not out of, the recess, and said body being molded in two halves which are joined and secured together by facing walls along a plane comprehending the vertical axis through the recess, each of said halves being further recessed adjacent the upper face to define half of an annular recess, and the means to permit the cap to be passed through the orifice, but not out of the recess comprising a centrally orificed disc provided with a plurality of inwardly radiating yieldable prongs inserted in the annular recess prior to the joinder of the two halves which form the body, whereby, when the syringe is to be employed, its capped needle is first inserted into the recess in the body through the means adapted to permit the cap to pass through the orifice, and the syringe is then withdrawn from the cap, thereby leaving the cap in the recess, and, when the syringe has been used and is ready for discarding, the syringe needle is re-inserted into the cap held in the recess down to where the means to secure the needle to the second end of the cylinder interlocks with the upper portion of the cap so that the entire syringe will be retained by the receptacle for discarding in a waste container or otherwise.

* * * * *